(12) United States Patent
Stam et al.

(10) Patent No.: US 8,523,884 B2
(45) Date of Patent: Sep. 3, 2013

(54) CLOSING MEANS FOR HOLLOW ORGANS

(75) Inventors: Sandra Monique Stam, Geetbets (BE); Rainer Desombre, Meerbusch (DE)

(73) Assignee: Q Medical International AG, Keltenbach (CH)

( * ) Notice: Subject to any disclaimer, the term of this patent is extended or adjusted under 35 U.S.C. 154(b) by 752 days.

(21) Appl. No.: 11/922,085

(22) PCT Filed: Jun. 13, 2006

(86) PCT No.: PCT/EP2006/063146
§ 371 (c)(1),
(2), (4) Date: Dec. 13, 2007

(87) PCT Pub. No.: WO2006/134106
PCT Pub. Date: Dec. 21, 2006

(65) Prior Publication Data
US 2009/0105735 A1    Apr. 23, 2009

(30) Foreign Application Priority Data

Jun. 15, 2005 (DE) .......................... 10 2005 027 809

(51) Int. Cl.
*A61B 17/08*        (2006.01)

(52) U.S. Cl.
USPC .............. 606/151; 606/191; 606/192; 600/37

(58) Field of Classification Search
USPC .............. 606/151, 157, 158; 623/1.11, 23.67, 623/23.65, 23.64–23.71; 600/37
See application file for complete search history.

(56) References Cited

U.S. PATENT DOCUMENTS

| 4,246,893 A | 1/1981 | Berson |
| 7,033,373 B2 * | 4/2006 | de la Torre et al. ............ 606/191 |
| 7,571,729 B2 * | 8/2009 | Saadat et al. .................. 128/898 |
| 7,717,843 B2 * | 5/2010 | Balbierz et al. ................. 600/37 |
| 7,776,061 B2 * | 8/2010 | Garner et al. .................. 606/151 |

(Continued)

FOREIGN PATENT DOCUMENTS

| DE | 197 51 733 A1 * | 12/1998 |
| WO | WO 2005/009305 A | 2/2005 |

OTHER PUBLICATIONS

Pier, Arnold, Laparoscopically-inserted band for reduction in stomach volume includes transdermal fluid balloon, tubing and port assisting controlled constriction, with perforations for precise, immovable fastening, Dec. 1998, Germany, Machine Translation.*

*Primary Examiner* — Corrine M McDermott
*Assistant Examiner* — Todd J Scherbel
(74) *Attorney, Agent, or Firm* — Miles & Stockbridge P.C.; David R. Shaffer, Esq.

(57) ABSTRACT

In a closing means for longitudinally extending hollow organs having a flexible wall and a passage, comprising at least one balloon-like chamber with a chamber volume, the chamber volume being variable by the supply of a fluid, and the passage of the hollow organ being partly or completely closable depending on the chamber volume, it is provided that a fastening device is arranged at the chamber, by which the chamber may be fastened to an outer part of the wall, parts of the wall of the hollow organ being adapted to be folded around the rectilinear chamber and to be fastened to the chamber or to each other such that the chamber, when in the fastened condition, is arranged in a fold in the wall of the hollow organ.

17 Claims, 6 Drawing Sheets

(56) References Cited

U.S. PATENT DOCUMENTS

| | | | |
|---|---|---|---|
| 2002/0055757 A1* | 5/2002 | Torre et al. | 606/192 |
| 2004/0059289 A1* | 3/2004 | Garza Alvarez | 604/96.01 |
| 2004/0193190 A1* | 9/2004 | Liddicoat et al. | 606/153 |
| 2005/0216040 A1* | 9/2005 | Gertner et al. | 606/151 |
| 2005/0283180 A1* | 12/2005 | Conlon | 606/192 |
| 2006/0252983 A1* | 11/2006 | Lembo et al. | 600/37 |
| 2009/0275942 A1* | 11/2009 | Ortiz et al. | 606/50 |

* cited by examiner

CLOSING MEANS FOR HOLLOW ORGANS

BACKGROUND OF THE INVENTION

The invention is directed to a closing means for longitudinally extending hollow organs comprising a flexible wall and a passage. The invention is further directed to a method for closing such hollow organs, or limiting the passage through. Such hollow organs may be organs in an animal body or a human body, for example.

Closing means for closing or constricting hollow organs are generally known. German Laid Open Publication DE-A-4109314, for example, describes an implantable device for closing a vessel, in particular a blood vessel, in the body of a living being. The device comprises a longitudinal flexible plate to be fastened around the vessel, wherein a plurality of communicating bubbles is provided on one side of the plate. After the plate has been fastened around the vessel, the bubbles are filled with a fluid so that they expand and press circularly against the walls of the vessel to close the same either partly or completely.

Moreover, means for constricting the stomach passage opening are known that take the form of so-called gastric bands. Gastric bands are used in treating pathologic overweight, the so-called morbid adiposity. Corresponding implants are also employed in so-called gastric restriction surgery.

Two types of such gastric restriction surgery have become widely accepted. The so-called "gastric banding" and the so-called "gastric bypass".

In "gastric banding", the entrance region of the stomach, the so-called stoma opening, is constricted by a gastric band in the form of an implanted plastic material band, e.g. of silicone, so that a stomach pouch is formed. The stomach pouch has only a small passage to the remaining part of the stomach, due to the constriction by the gastric band, so that a patient will feel saturated already after having consumed a small amount of food or that he can consume only a certain amount of food in a certain period of time. However, there is a risk that the constricted stomach pouch becomes bulged and expands. With all gastric bands, there is a further risk of the band becoming displaced or penetrating into the stomach wall.

Especially when using the above mentioned annular closing means having a circularly expandable part, so-called pressure necroses may occur because of the pressure acting on the wall of the organ.

With a "gastric bypass", the upper part of the stomach is separated by means of retaining staple lines, so that the lower stomach part and the duodenum are completely deactivated. The upper stomach part is connected with a loop of the small intestine pulled up to that stomach part and serving as a bypass for the remaining stomach and the duodenum. This kind of surgery is deemed irreversible, which is critical in the event of future complications such as malabsorptions. Further, the separated stomach part and the duodenum can no longer be reached endoscopically for diagnosis or treatment.

In a development of the "gastric bypass", a combination of this surgical method and the use of a gastric band has been tested. Here, a part of the stomach is pinched off entirely with a gastric band and a corresponding bypass connection of the upper stomach part with the small intestine is established. This method is not generally irreversible, but the known problems in connection with gastric bands, e.g. pressure necroses or erosion, still exist. The gastric band must also exert high pressure on the stomach wall in order to complete the closure of the stomach passage.

For the above described method, practice has shown that, for a complete closure of the stomach part, a gastric band has to exert so high a pressure on the stomach walls that necroses and a penetration into the stomach wall necessarily have to occur so that the method is not practicable. The gastric band in contact with the small bowel loop can perforate at that level too.

Therefore, it is an object of the present invention to provide a closing means of the kind mentioned at the beginning, wherein, while avoiding the above mentioned disadvantages, a passage of a hollow organ with a flexible wall, especially in an animal body or a human body, may be closed reversibly.

SUMMARY OF THE INVENTION

According to the invention, a closing means for longitudinal hollow organs of a human or animal body, which organ has a flexible wall and a passage, comprises at least one chamber having a chamber volume. The chamber volume is variable through the supply of a fluid so that the passage of the hollow organ may be closed partly or entirely as a function of the chamber volume. The chamber extends substantially rectilinearly and is of longitudinal configuration. The chamber comprises a fastening device by which the chamber may be fastened to an exterior part of the hollow organ wall, wherein portions of the hollow organ wall are adapted to be folded about the rectilinear chamber and to be fastened to the chamber and/or to each other such that, when in the fastened condition, the chamber is arranged in a fold (plicature) of the hollow organ wall. In other words, the hollow organ is folded in the longitudinal and transversal directions such that the chamber can be arranged in the fold thus formed. Thereafter, the chamber can be fastened to the hollow organ. By filling the chamber and expanding the chamber volume, the balloon-like chamber exerts pressure on the wall of the hollow organ from one side and can close a passage of the hollow organ completely. This has the advantage that pressure acts on the wall of the hollow organ only from one side and that less pressure is necessary for a complete closure of the hollow organ. Moreover, due to the unilateral pressure on the hollow organ, there is no longer any risk of a constriction of the hollow organ. Using the fastening device, the closing means may be fixed at the hollow organ so that the closing means can not slip. Pressure necroses, occurring frequently when gastric bands are used, for example, are avoided because of the lower pressure acting only on one side of the hollow organ. Since, when closing the passage, the walls of the passage in the hollow organ come to contact each other due to the pressure acting on the one side of the passage wall, less pressure is required for closing the passage. Further, no folds are formed in the walls, as is the case with a closing means acting circularly on the walls of a hollow organ.

Preferably, the chamber is adapted to be fastened on the outer side of the wall in the longitudinal direction, such that the fastened chamber extends along the longitudinal direction of the hollow organ and in parallel with the hollow organ. Here, the hollow organ is folded longitudinally so that the chamber is located in the longitudinal fold of the hollow organ. This is advantageous in that the wall of the hollow organ is pressurized over a relatively long section and the passage of the hollow organ is thus closed over the entire section. This requires less pressure for closing the hollow organ and the risks of constrictions of the hollow organ or of a cutting of the closing means into the wall of the hollow organ are decreased.

As an alternative, the chamber may be fastened to the outer side of the hollow organ along the transversal direction so that the chamber extends transversal to the hollow organ, when fastened. This kind of fastening is particularly advantageous with relatively thin hollow organs, the hollow organ also being folded in the transversal direction of the hollow organ.

Preferably, the fold in the wall of the hollow organ has at least one fold edge and the fastening device is at least one fastening strip protruding radially from, the chamber such that at least one fold edge of the hollow organ may be fastened to the fastening device and to the wall of the hollow organs.

In this case, it is particularly advantageous if two fold edges are formed by the folding so that the hollow organ may be fastened from both sides to the fastening strip by a respective one of the fold edges. The fastening strip preferably forms a separation layer between the fold edges of the hollow organ fastened to the fastening strip. Thus, it is possible to fasten the closing means to the hollow organ in a particularly simple manner and to fix the fold of the hollow organ at the same time. Here, the fastening strip serves as a separation layer between the folding edges so that a later detaching of the fold edges from each other by disconnecting the fastening means can be done in a particularly simple manner. With hollow organs of an animal body or a human body fusion and adhering of the fold edge or the fold edges are prevented.

In a particularly preferred embodiment, the fastening device is comprised of two spaced parallel fastening strips, a fold edge of the hollow organ being adapted to be fastened to the side of a fastening strip averted from the adjacent fastening strip, such that the spacing between the fold edges of the hollow organ fastened to the fastening strip may be determined by the spacing between the fastening strips, wherein the spacing between the fastening strips is preferably variable. Thus, it is possible to also close hollow organs having a relatively small circumference with a closing means arranged in the longitudinal direction of the hollow organ, since the fold of the hollow organ does not have to enclose the entire closing means. Moreover, a variable spacing between the fastening strips offers the possibility to control the tensile force acting on the fold of the hollow organ. To this effect, for example, eyelets may be arranged on the fastening strip side facing the adjacent fastening strip, the spacing between the fastening strips being variable via a suture cord extending through the eyelets.

The fastening device may comprise holes for the engagement of fastening means. Thus, it is possible to fasten the closing means to the hollow organ in a particularly simple manner, for example using a suture passing through the holes or clips extending through the holes.

Preferably, the fastening strip extends at least over the length of the chamber.

In an advantageous embodiment of the invention, the fastening strip comprises discontinuities along the longitudinal direction. Thus, the chamber is both torsion elastic and transversely elastic despite the fastening strip so that the chamber is readily adaptable to slightly bent hollow organs.

The balloon-like chamber may be adapted to be sewed or clamped to the wall of a hollow organ by means of the fastening device.

In a particularly preferred embodiment, at least one tube connects the chamber to at least one fluid port such that the chamber may be filled with fluid through the fluid port. Thus, it is possible to change the filling volume of the closing means at a site remote from the closing means using the fluid port. When using such a closing means in a human or animal body, the fluid port may be implanted subcutaneously, for example, so that the chambers of the closing means can be filled or emptied using a syringe to pierce into the fluid port through the skin. The fluid circuit can be closed (pump and fluid reservoir inside the body) or open to the exterior of the body (port chamber, aso).

In the longitudinal direction of the chamber, the fastening device may have at least one portion projecting beyond the chamber. This allows for a particularly advantageous fastening of the closing means to the hollow organ. For example, a fastening device in the form of a fastening strip can protrude in the longitudinal direction of the chamber on one or both sides, so that the chamber need not necessarily have the same length as the fold of the hollow organ. The fastening strips may serve to fasten the closing means in the fold over the entire length and to fix the fold.

In prolongation of the chamber, a plate-shaped separating tab may be provided which, in the fastened condition of the closing means, forms a separating intermediate layer for adjacent parts of the hollow organ. When using the closing means in a human or animal body, there is a risk that the folded walls of the hollow organ grow together, for example. By employing such a plate-shaped separating tab, the folding of the hollow organ may be longer than the chamber of the closing means, the plate-shaped separating tab forming a separating intermediate layer in the region of the fold of the hollow organ not filled by the chamber, so that a fusion of the walls of the hollow organ is prevented.

Preferably, the tube for filling the chamber is guided at least partly in the fastening device or fixed to the fastening device. Thus, it is possible to lead the tube to the chamber in a simple manner. This can act as a skeleton for a very flexible chamber when it is empty.

In a preferred embodiment, the chamber is divided into sub-chambers of equal or different sizes. This allows to safely close irregularly shaped hollow organs, too, by filling the sub-chambers of the closing means differently, so as to exert a varying pressure on the wall.

In a particularly preferred embodiment, the chamber has a flexible partition dividing the chambers in two sub-chambers, wherein two spaced fastening strips of the fastening device are commonly arranged at the wall of one of the sub-chambers, such that the spacing between the fastening strips may be varied by a different degree of filling of the sub-chambers. Thus, it is possible to vary the tensile forces acting on the fold by changing the spacing between the fastening strips, which in turn is varied by a differential filling of the sub-chambers.

The tube connected with the balloon-like chamber may have a plurality of channels, each terminating in a sub-chamber of the closing means and each being connectable with a space of a fluid port having a plurality of spaces or with a respective one of different fluid ports. This allows to vary the pressure in the different sub-chambers individually and to vary the closing of the hollow organ or the tensile force acting on the fold of the hollow organ.

When two parallel fastening strips are provided, the spacing between the fastening strips may be variable by an expansion of the chamber wall resulting from a different degree of filling of the chambers or the sub-chambers. In this manner, too, the tensile force acting on the fold can be influenced.

In a method for a partial or complete closing of a passage of a longitudinal hollow organ with a flexible wall in a human or animal body, first, a chamber is placed against a portion of the wall of the hollow organ. Thereafter, the hollow organ is folded such that the hollow organ at least partly surrounds the chamber and that at least one fold edge is formed.

At least one fold edge is fastened such that the chamber is situated in the fold of the hollow organ. Then, the chamber is fastened to the hollow organ. The fastening of the chamber may also be done before the folding of the hollow organ, or it may be effected by fastening the fold edges to the outer side of the wall of the hollow organ.

By filling the chamber with a medium such that the volume of the chamber changes, the balloon-like chamber exerts pressure on the wall of the hollow organ to close the passage of the hollow organ.

Preferably, the chamber is formed using a closing means described above.

Other advantageous embodiments of the method are mentioned in the dependent claims.

The above described closing means may further be used in surgery when performing a gastric bypass. It can be used to control the "continence" of any hollow organ.

The following is a detailed description of the invention with reference to the drawings.

DETAILED DESCRIPTION OF THE PREFERRED EMBODIMENTS

Figure 1:
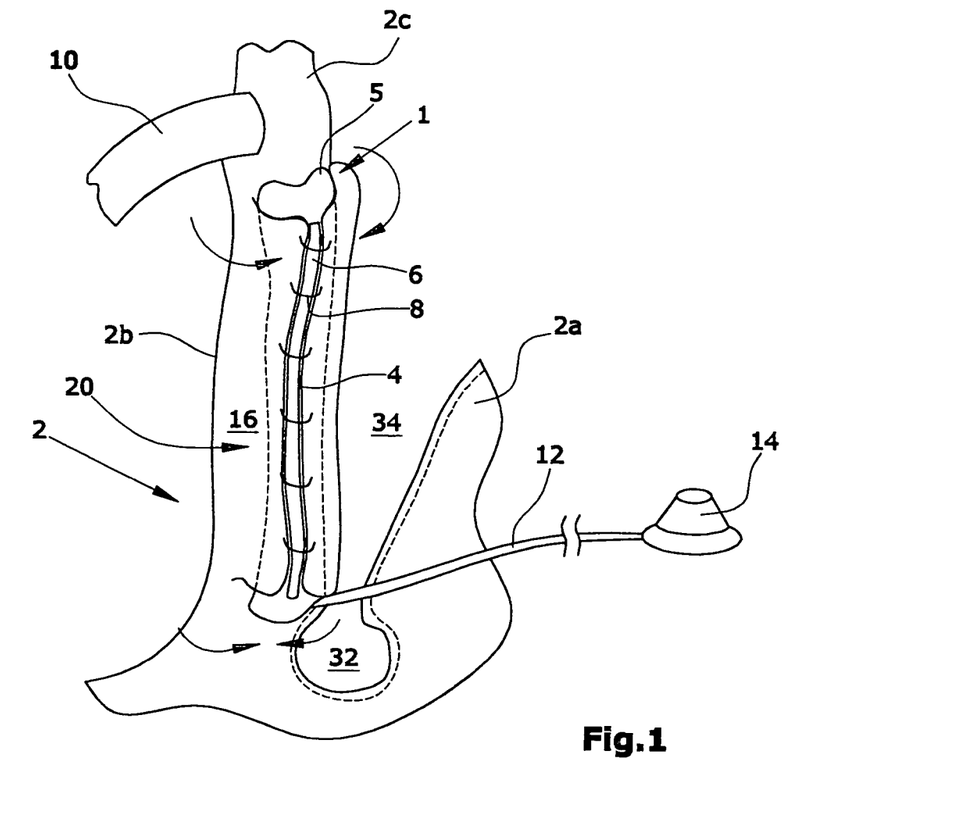
FIG. 1 is a perspective schematic illustration of a closing means according to the present invention, which has been sewn into a hose-shaped portion of a stomach along the longitudinal direction.

FIG. 1 is a perspective schematic illustration of a stomach 2 to which a bypass has been applied by means of a small intestine loop 10. The stomach 2 has been divided into a bag-like part 2a and a hose-shaped part 2b. The tubular part 2b of the stomach has been folded to a plicature into which a closing means 1 according to the present invention has been inserted. The fold edges 4 of the plicature of the hose-shaped part 2b of the stomach 2 are fastened to a fastening strip 6 projecting radially from a balloon-like chamber 5 of the closing means 1 extending in the longitudinal direction.

The fastening has been effected with fastening means 8, e.g. a suture or clips. Above the closing means 1 a small intestine loop 10 is connected to the upper section 2c of the hose-shaped part 2b of the stomach 2 to form the bypass. At its bottom end, the chamber 5 of the closing means 1 is connected to a fluid port 14 through a tube 12. Via the fluid port 14 and the tube 12, the chamber can be filled with a medium, in particular a fluid. By filling the chamber 5 with a medium, the chamber volume of the balloon-like chamber 5 is enlarged so that the chamber presses against the outer side of the wall of the tubular part 2b of the stomach 2, thereby closing the passage (not illustrated in FIG. 1) of this part 2b of the hollow organ.

Figure 2A:
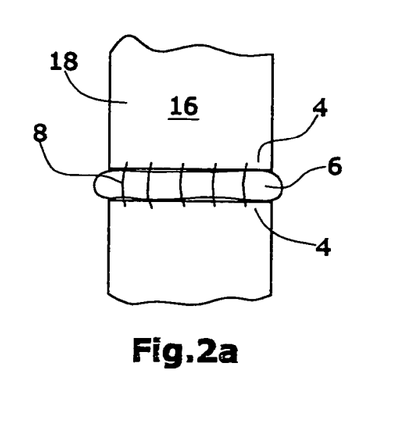
FIGS. 2a and 2b are schematic illustrations of another embodiment of the present closing means arranged in a transverse fold of a hollow organ.
Figure 2B:
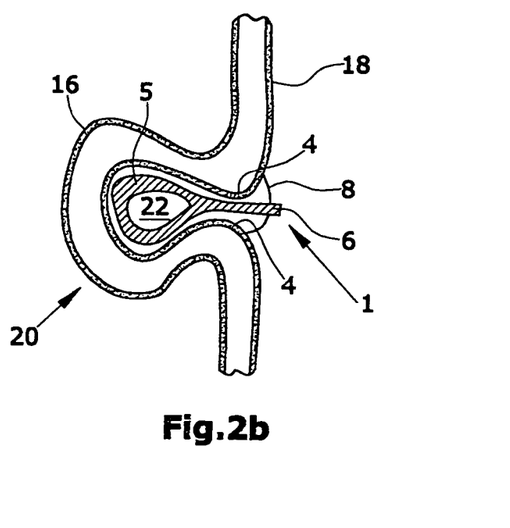

FIGS. 2a and 2b illustrate a second embodiment of a closing means of the present invention. A hollow organ 18, which is relatively thin compared to the hollow organ illustrated in FIG. 1, has been folded to a plicature 20 transversal to the hollow organ 18. A closing means 1 is positioned in the fold 20, as is best seen in the sectional view in FIG. 2b. The closing means comprises a chamber 5 with a variable chamber volume 22. By fastening means 8 in the form of a suture or clips, the fold edges 4 of the plicature 20 of the hollow organ 18 are fastened to each other or to the fastening device 6 of the closing means 1 such that the fastening device 6 forms an intermediate layer between the fold edges 4. This is advantageous in that there is no risk of parts of the wall 16 of the hollow organ 18 adhering or growing together at the fold edges 4. By a simple detachment of the fastening means 8, the closing means 1 can thus be removed from the plicature 20.

Figure 3:
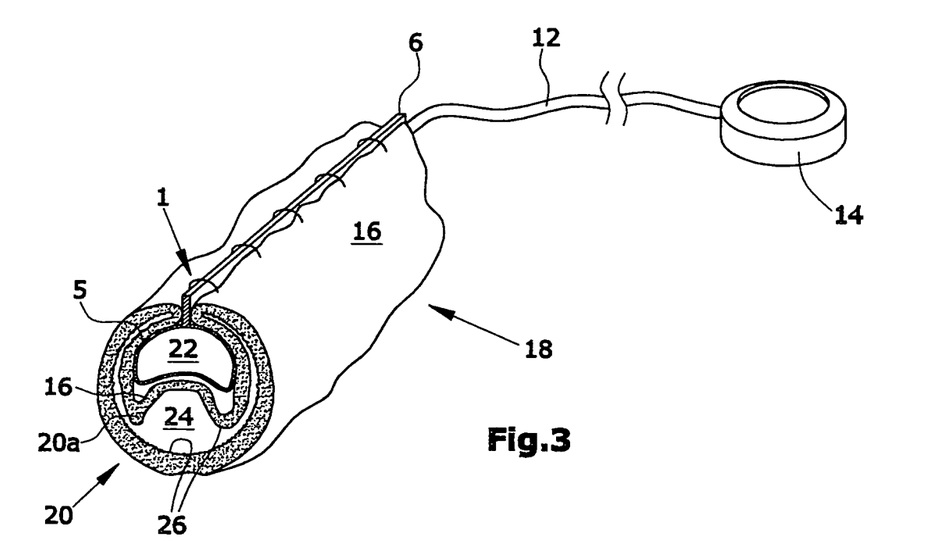
FIG. 3 is a schematic section through an unfilled closing means inserted into the fold of a hollow organ.

FIG. 3 illustrates another embodiment of the present closing means. The closing means is situated in the plicature 20 of a hollow organ folded in the longitudinal direction. The volume 22 of the chamber 5 has not yet been filled with a fluid in the condition illustrated in FIG. 3. The closing means 1 is connected to a fluid port 14 through a tube 12. By filling the chamber 5 with a fluid through the fluid port 14, the chamber volume 22 expands, presses against the wall 16 of the inner part 20a of the plicature 20 and presses the inner sides 26 of the hollow organ 18 against each other so that the passage 24 of the hollow organ 18 is closed. With organs of an animal or human body, the inner sides 26 of a corresponding hollow organ 18 are mucous membranes so that there is no risk of the inner sides 26 growing together. By emptying the balloon-like chambers 5, the passage 24 of the hollow organ 18 can be opened again in a simple manner.

Figure 4:
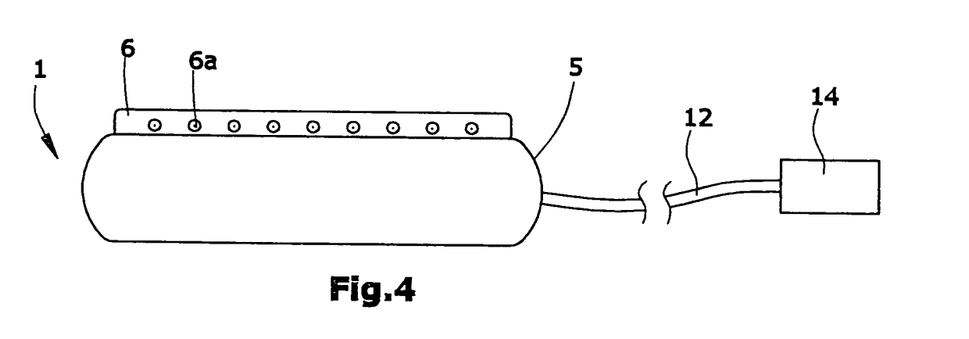
FIGS. 4 to 9 show different embodiments of the present closing means in schematic side view with different forms of fastening devices.

FIGS. 4 to 10 schematically illustrate different embodiments of a present closing means. FIG. 4 shows an embodiment of the present closing means 1 as it is illustrated, for example, in the embodiments of FIGS. 1, 2a, 2b and 3 in the inserted condition. The closing means 1 has a balloon-like chamber 5 from which a fastening device 6 in the form of a fastening strip protrudes radially. The fastening strip 6 has holes 6a through which the fastening means for fastening the closing means 1 may be passed. At one end of the chamber 5, a tube 12 is provided connecting the balloon-like chamber 5 with a fluid port 14. Preferably, the entire closing means 1 is formed from one material, e.g. a stretchable plastic material like silicone.

Figure 5:
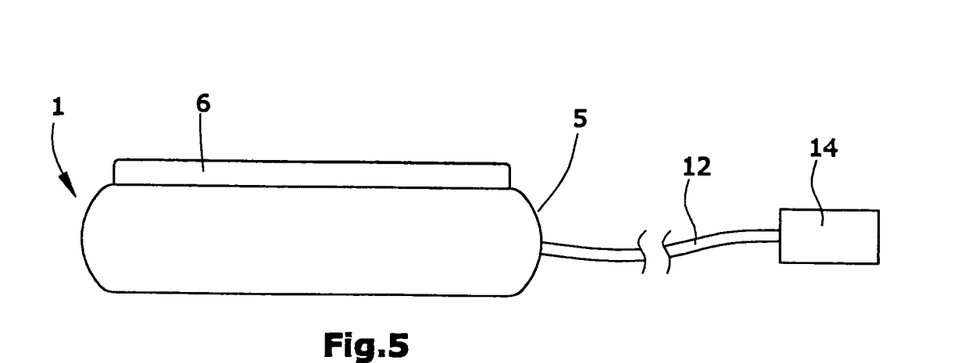

The embodiment of the present closing means 1 illustrated in FIG. 5 is similar to the embodiment in FIG. 4, except for the fastening device 6 having no holes. To fasten a closing means 1 according to this embodiment, fastening means are pierced directly through the material of the fastening device 6. This may be advantageous, if a fixed spacing between the fastening means, as it is the case for the closing means 1 of FIG. 4 due to the predefined spacing of the holes 6a, cannot be realized while fastening the closing means 1.

Figure 6:
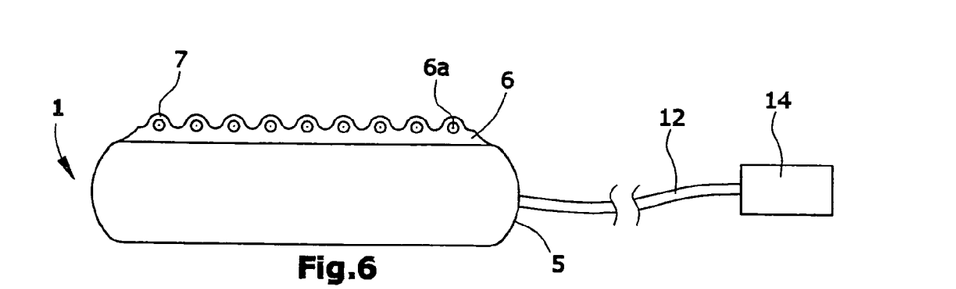

FIG. 6 illustrates another embodiment of a closing means 1, wherein the fastening device 6 is a fastening strip which is provided with eyelets 7 having holes 6a.

Figure 7:
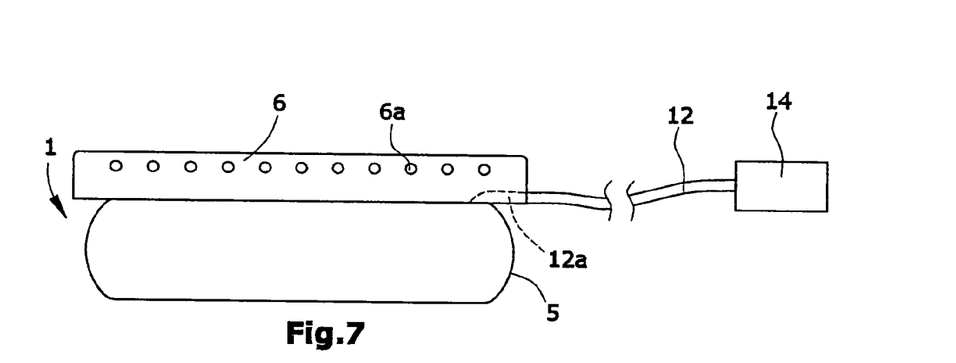

In the embodiment of a present closing means illustrated in FIG. 7, the fastening device 6 in the form of a fastening strip is provided with holes 6a, the fastening device 6 projecting beyond the chamber 5 in the longitudinal direction. This is advantageous in that, when such a closing device is used in a relatively long plicature of a hollow organ, the chamber 5 need not extend over the whole length of the fold, wherein the fold edges of the fold of the hollow organ can be fastened over the entire length of the fold to advantageously fix the fold and to fasten the closing means 1 to the fastening strip 6. In the embodiment of FIG. 7, a section 12a of the tube 12 is guided in the fastening strip 6 so that the balloon-like chamber 5 can be connected with the tube 12 in a simple manner.

Figure 8:
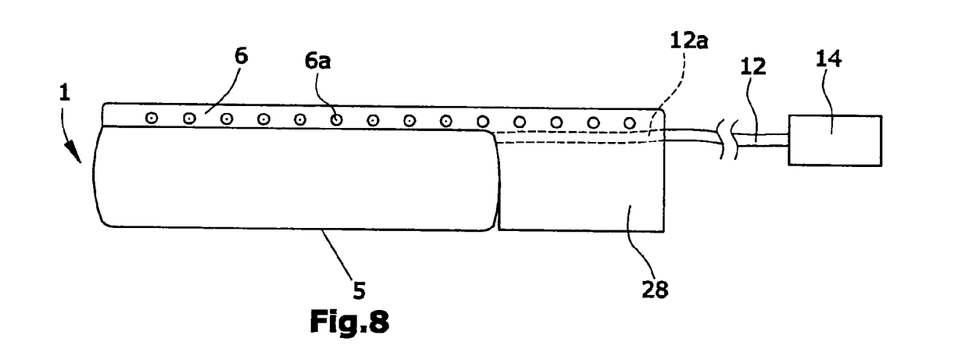

In prolongation of the chamber 5, a closing means 1 according to FIG. 8 is provided with a plate-shaped separating tab 28 which, in the fastened condition of the closing means 1, forms an intermediate layer between walls of the hollow organ in a plicature. Thus, it is possible to insert the closing means 1 into the fold of a hollow organ that is substantially longer than the balloon-like chamber 5 of the closing means 1. This is advantageous, especially when applying such a closing device to an organ in a human or animal body, since the outer sides of such an organ tend to grow together. By providing a plate-shaped separating tab 28, an intermediate layer is formed in the fold between the outer sides of the wall of the hollow organ in the portion not filled by the chamber 5, so that the risk of the outer sides of the walls growing together is reduced in this portion. Here, as illustrated in FIG. 8, the fastening device 6 may extend along the plate-shaped separating tab 28. It is particularly advantageous if a section 12a of the tube 12 is guided in or along the plate-shaped separating tab 28 to connect the balloon-like chamber 5 with a fluid port 14.

Figure 9:
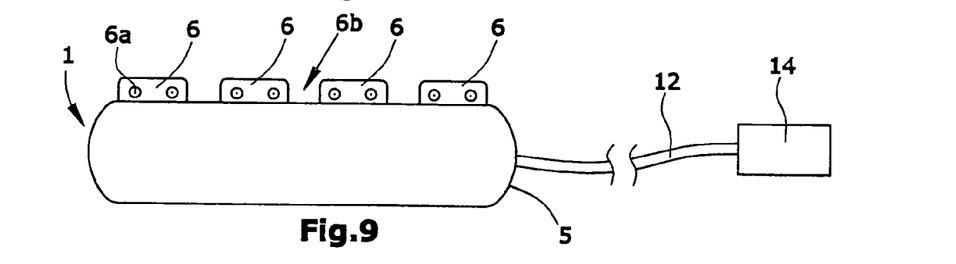

FIG. 9 illustrates another embodiment of a present closing means 1. A fastening device 6 protrudes radially from the balloon-like chamber 5, taking the form of a fastening strip with a plurality of discontinuities. The fastening strip is provided with holes 6a to pass fastening means there through. Due to the discontinuities 6b in the fastening device 6, the closing means 1 is substantially more torsion elastic and also more elastic in the transversal direction as compared to the embodiment of the closing means 1 illustrated in FIG. 4, since, in the embodiment of FIG. 4, the fastening device 6 acts as a stiffening rib. Thus, the embodiment of the closing means 1 illustrated in FIG. 9 can also be employed with curved hollow organs, because it can adapt to the curvature of the hollow organ.

Figure 10:
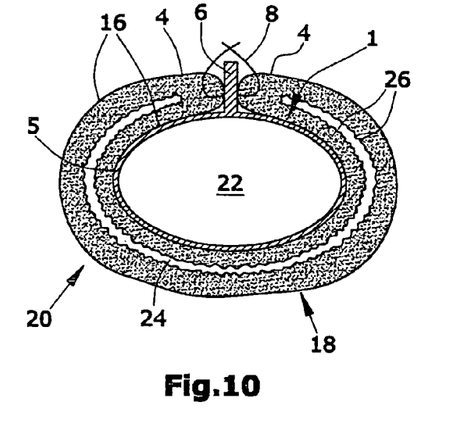
FIGS. 10 and 11 are schematic sectional views on filled closing means of different cross sections, each arranged in a fold of a hollow organ.
Figure 11:
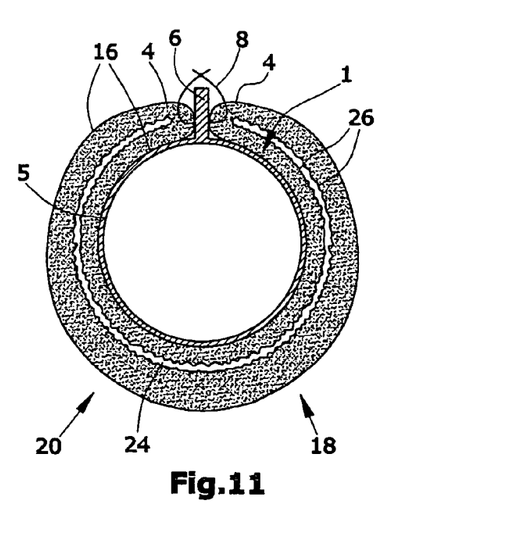

FIGS. 10 and 11 illustrate two embodiments of a present closing means 1 located in a fold of a hollow organ. The embodiment illustrated in FIG. 10 has a balloon-like chamber with an oval cross section, whereas the embodiment illustrated in FIG. 11 has an almost round chamber cross section. Using fastening means 8 passed through the fastening device 6, the chambers are each connected to the fold edges 4 of the fold 20 and thus to the hollow organ 18. At the same time, the fold 20 is fixed by this fastening. In both embodiments, the chambers 5 are almost completely filled with a fluid so that the chamber volume 22 is expanded almost to the maximum. The chamber 5 presses against the walls 16 of the hollow organ 18 located in the oner part of the fold 20, so that the inner walls 26 of the hollow organ are pressed against each other and close the passage 24 of the hollow organ 18.

Figure 12:
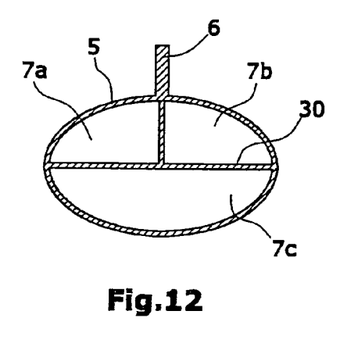
FIGS. 12 and 13 are schematic sectional views on present closing means with different sub-chamber arrangements.
Figure 13:
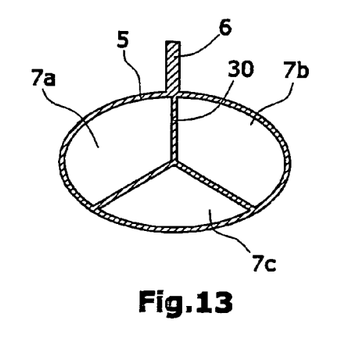
Figure 14:
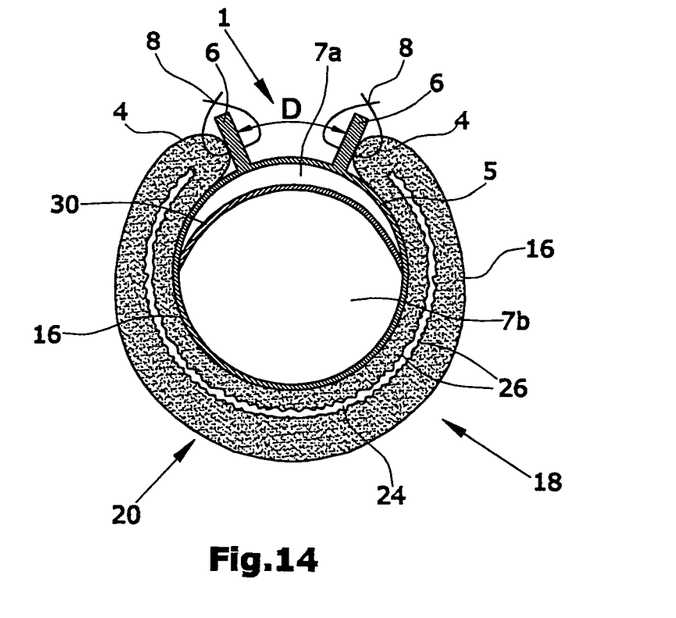
FIG. 14 is a schematic section through another embodiment of a present closing means with two fastening strips in the fold of the closing means in the fastened condition.

As illustrated in FIGS. 12 and 13, the chamber 5 may be divided into several sub-chambers 7a, 7b, 7c. Here, as illustrated in FIG. 12, the sub-chambers 7a, 7b, 7c may have different sizes, but they may also be of equal size, as illustrated in FIG. 14. The sub-chambers 7a, 7b, 7c may be connected to a plurality of fluid ports via a tube having a plurality of channels, so that the sub-chambers 7a, 7b, 7c can be filled differently. Both the fluid chosen and the degree of filling may be different, so that the pressure acting on the corresponding parts of the wall of the hollow organ can be varied. The division of the balloon-like chamber does not necessarily have to be in the longitudinal direction, as illustrated in FIGS. 12 and 13, but may also be transverse to the longitudinal direction of the closing means, so that a plurality of successively arranged sub-chambers forms the chamber 5.

In an embodiment according to FIG. 14, the closing means 1 comprises a chamber 5 divided into two sub-chambers 7a and 7b. The sub-chambers 7a and 7b have a slightly curved elastic intermediate wall 30. On the outer side of the wall of the sub-chamber wall 7a, a fastening means 6 in the shape of two parallel fastening strips extending radially from the balloon-like chamber 5 is arranged. The fastening strips 6 extend at a distance D from each other. On the sides averted from the adjacent fastening strip, the fold edges 4 of the fold 20 of the hollow organ 18 is fastened to the fastening strips 6, respectively, so that the tensile force acting on the fold 20 can be determined by the distance D between the fastening strips 6. By a different degree of filling in the sub-chambers 7a and 7b, the distance D between the fastening strips 6 can be varied, so that even after the placing of the closing means 1 into the plicature 20 of the hollow organ 18 the tensile force acting on the plicature 20 can be varied. Should the closing means 1 be connected to one or a plurality of fluid ports 14 through a tube 12 with a plurality of channels (both not illustrated in FIG. 14), the adjustment of the distance D between the fastening strips 6 can be effected from a location remote from the closing means 1.

The sides of the fastening strips 6 respectively facing the adjacent fastening strip 6 may be provided with eyelets 7 (not illustrated in FIG. 14) through which the distance D and thus the tensile force acting on the plicature 20 can be adjusted by means of a suture cord after the closing means 1 has been placed into the plicature 20 of the hollow organ 18.

The closing means described above may not only be employed in closing a stomach part, but also for organs with tubular structures such as the small and the large intestine.

The above described closing means may be used, for example, in a "gastric bypass" surgical method. Such a method will now be described with reference to FIG. 1.

First the stomach 2 is "tailored" and the exposed stomach wall edges are sutured or clamped such that the stomach 2 is divided into two parts 2a, 2b that are in communication with each other, at least one part 2b being configured in hose-shaped manner. Suitable methods for cutting are, for example, the Mason gastro-plastic surgery or the MacLean gastro-plastic surgery. Here, a stapler with a circular cross section is applied in the lower stomach part and actuated. Thereafter, a longitudinally extending stapling device, e.g. of the type endoGIA, is applied through the window 32 thus formed and is actuated in the cephalic direction to make a cut 34 while simultaneously suturing in about a vertical direction.

The next step is to fold the hose-shaped stomach part 2b into a plicature 20, into which a closing means 1 described above is inserted and fastened therein. Thereafter, the fold edges 4 of the plicature 20 are fastened to fix the plicature 20. The closing means 1 may also be fastened together with or after the fixation of the fold edges 4 to the plicature 20.

In a further step, a small intestine loop 10 is connected with the stomach 2c in the cephalic direction above the closing means 1 so as to form a bypass. This method is similar to the placing of a Roux-en-Y-Gastric-Bypass.

Thereafter, the chamber 5 of the closing means is connected to a fluid port 14 via a tube 12.

The order of the surgical steps is not invariably fixed. For example, a part of the stomach may be folded first and the closing means is arranged in the plicature and fastened to the stomach as described above. Then, the stomach is tailored along the closing means and the exposed stomach wall edges are sutured or clamped such that the stomach is divided into two parts in communication with each other. One part is hose-shaped and comprises the plicature formed before and the closing means arranged in the plicature.

The above described surgical methods have the advantage that the gastric bypass is reversible. By emptying the chamber of the closing means, the hose-shaped part of the stomach is opened so that the same may become functional again. Through a tube connecting the chamber with a fluid port provided under the skin, the medium may be drawn from the chamber through the fluid port, so that, in the event of complications such as malabsorptions or for endoscopic examination, for example, the metabolic pathway through the stomach, the intestines and the duodenum can be opened relatively fast.

The above described closing means may also be used in a surgical method combining stomach reduction and resection of the fundus. Such a method will now be described with reference to FIG. 15.

Figure 15:
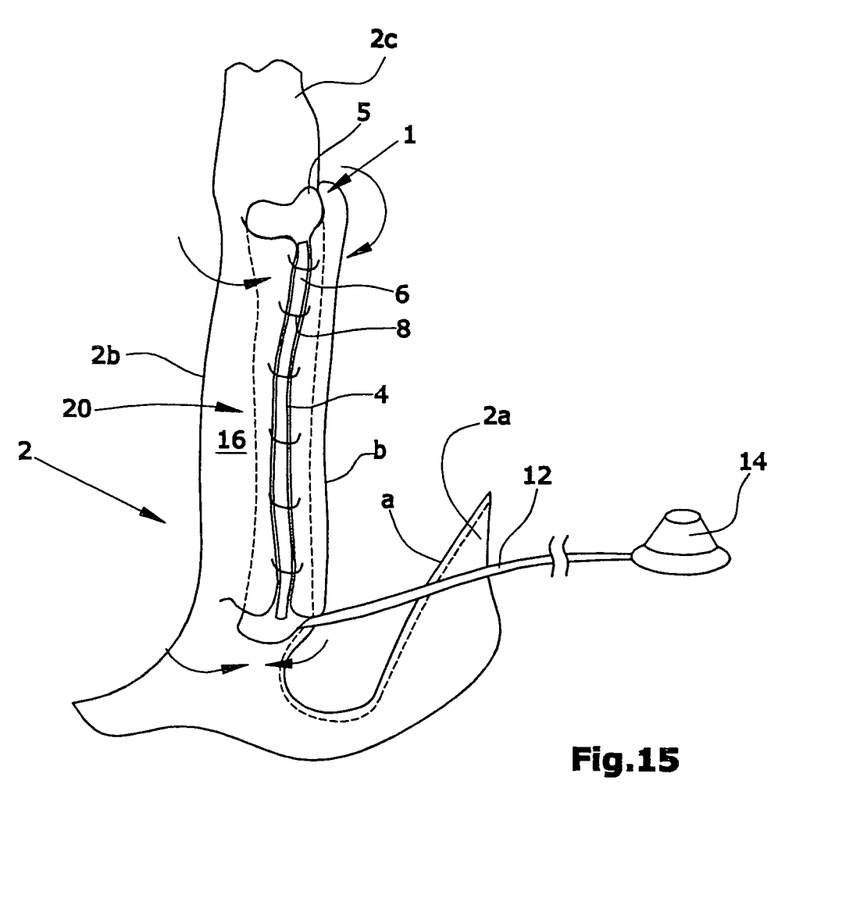
FIG. 15 is a schematic perspective view and illustrates a surgical method combining stomach reduction and resection of the fundus.

First the stomach 2 is tailored and the exposed stomach wall edges are sutured or clamped such that the stomach 2 is divided into parts 2a and 2b, being in communication with each other, at least one part 2b being configured in a hose-shaped manner. Thereby, a part of the stomach 2 is surgical removed and therefore the volume of the stomach is reduced.

The next step is to fold the hose-shaped stomach part 2b into a plicature 20, into which a closing means 1 described above is inserted and fastened therein. Thereafter, the fold edges 4 of the plicature 20 are fastened to fix the plicature 20. The closing means 1 may also be fastened together with or after the fixation of the fold edges 4 to the plicature 20.

In a further step the stomach part 2a is fixed to the stomach part 2b by fixing the stomach wall edge (a) to an outer edge (b) of the plicature 20.

Thereafter, the chamber 5 of the closing means is connected to a fluid port 14 via a tube 12.

The order of the surgical steps is not invariably fixed. For example, a part of the stomach may be folded and the closing means is arranged in the plicature and fastened to the stomach as described above. Then the stomach is tailored along the closing means and the exposed stomach wall edges are sutured or clamped such that the stomach is divided into two parts in communication with each other. By using the above-described closing means with this method it is possible to restrict the size of the stomach entrance (cardia) by filling the closing means with the fluid via the fluid port 14. Further, if a gastric bypass is needed, it is easily possible to form a bypass by connecting a small intestine loop with the stomach 2c in cephalic direction above the closing means 1. In this case the closing means is used for closing the passage through the stomach entrance.

In a method for partly or completely closing a passage of a longitudinally extending hollow organ with a flexible wall in a human or animal body, the following steps are provided:
placing a rectilinear chamber to the side of an outer wall of the hollow organ,
folding the hollow organ such that the hollow organ encloses the chamber at least partly and that at least one fold edge is formed,
fastening a fold edge such that the chamber is situated within a fold of the hollow organ,
fastening the chamber to the hollow organ,
filling the balloon-like chamber with a fluid such that the volume of the chamber changes and the chamber presses against the wall of the hollow organ so as to close the passage of the hollow organ.

Moreover, when folding the hollow organ, two fold edges may be formed, the fold edge or the fold edges being adapted to be fastened to the chamber.

Alternatively or additionally, the fold edges may be fastened to each other.

The chamber may comprise a fastening device, preferably a fastening strip, at which the fold edge or fold edges may be fastened.

In particular, a respective fold edge may be fastened to the fastening device from both sides.

The fastening of the chamber to the hollow organ may be effected by fastening the fold edge or the fold edges to the chamber.

Preferably, the fold edges are fastened to two parallel spaced fastening strips such that the distance between the fold edges of the hollow organ fastened to the fastening strips may be determined by the distance between the fastening strips, the distance between the fastening strips preferably being variable.

Here, the following method step may be provided:
connecting the fastening strips with a suture cord passing through the eyelets, while simultaneously adjusting the tensile forces acting on the hollow organ by determining the distance between the fastening strips using the suture cord passing through the eyelets.

In a method for placing a gastric bypass, the following steps are provided:
cutting the stomach of a human or animal body and suturing or clamping the exposed stomach wall edges such that the stomach is divided into two parts which are in communication with each other, at least one part being hose-shaped,
laying the hose-shaped stomach part to form a plicature with two fold edges,
arranging a closing means in the plicature,
fastening the fold edges to each other to fix the plicature,
fastening the closing means to the hose-shaped stomach part,
connecting a small intestine loop to the hose-shaped stomach part in the cephalic direction above the closing means,
filling the closing means with a fluid such that the hose-shaped stomach part is closed.

In an alternative method for placing a gastric bypass, the following steps are provided:
folding a part of the stomach of a human or animal body to form a plicature with two fold edges,
arranging a closing means in the plicature,
fastening the fold edges at each other to fix the plicature,
fastening the closing means to the stomach part,
cutting the stomach along the folded stomach part and suturing or clamping the exposed stomach wall edges such that the stomach is divided into two parts that are in communication with each other,
connecting a small intestine loop with the stomach in the cephalic direction above the folded stomach part,
filling the closing means with a fluid such that the folded stomach part is closed.

In both methods, the step of cutting the stomach preferably is a gastro-plastic surgery step, preferably a Mason or MacLean gastro-plastic surgery step.

Here, the fold edges may be fastened to each other to fix the plicature and to the closing means for a simultaneous fastening of the closing means to the stomach part, preferably by suturing or clamping.

Although a preferred embodiment of the invention has been specifically illustrated and described herein, it is to be understood that minor variations may be made in the apparatus without departing from the spirit and scope of the invention, as defined by the appended claims.

We claim:

1. A closing means (1) for longitudinally extending hollow organs (18) having a flexible wall (16) and a passage (24), comprising
at least one chamber (5) with a chamber volume, the at least one chamber (5) extending rectilinearly and having a longitudinal configuration and a circumference,
the chamber volume (22) being variable by a supply of a fluid,
and the passage (24) of the hollow organ being partly or completely closable depending on the chamber volume (22),
a fastening device (6) being connected to and protruding radially from only one longitudinal side of an exterior of the chamber (5) for fastening the chamber (5) to an outer part of the wall of the hollow organ, wherein in a fastened condition of the fastening device (6), the chamber (5) being adapted to be arranged in a fold (20) in the wall of the hollow organ, the fastening device (6) including only one fastening strip (6) having two sides and an edge around and connected between a periphery of each side, the fastening strip being connected along a first longitudinal portion of the edge to and extending radially from the circumference and the only one longitudinal side of the chamber (5) and each side of the fastening strip being fastenable to a respective fold edge (4) of the hollow organ (18).

2. The closing means of claim 1, wherein the rectilinear chamber (5) is adapted to be fastened to the outer side of the wall along a longitudinal direction of the hollow organ, such that the chamber (5), when fastened, extends along the longitudinal direction of the hollow organ (18) and parallel to the hollow organ (18).

3. The closing means of claim 2, wherein the fastening device (6) has at least one part extending beyond the chamber (5) in a longitudinal direction of the chamber (5).

4. The closing means of claim 1, wherein the fastening device (6) comprises holes (6a) for the engagement of a fastening means (8).

5. The closing means of claim 1, wherein the fastening strip (6) extends over at least a length of the chamber (5).

6. The closing means of claim 1, wherein the chamber (5) is adapted to be sutured or clamped to an outer side (16) of the hollow organ (18) by means of the fastening device (6).

7. The closing means of claim 1, wherein the chamber (5) is connected to at least one fluid port (14) through at least one tube (12), such that the chamber (5) may be filled with fluid through the fluid port (14).

8. The closing means of claim 7, wherein the tube (12) is at least partly guided in the fastening device (6) or fastened to the fastening device (6).

9. The closing means of claim 1, wherein the closing means is formed from a single material.

10. The closing means of claim 9, wherein the single material comprises silicone.

11. The closing means of claim 1, wherein the chamber (5) is outwardly expandable and inwardly deflatable in all directions.

12. A closing means (1) comprising:
at least one longitudinally extending and rectilinear chamber (5) having a variable chamber volume, a circumference, a length, an outer surface and first and second ends, the chamber (5) being expandable in all directions, and
a fastening device (6) connected to and protruding radially from only one longitudinal side of and extending longitudinally along the length of the chamber (5) from adjacent the first end to adjacent the second end, the fastening device (6) including only one two-sided fastening strip (6) with an edge around and connected between a periphery of each side, the fastening strip being connected along a first longitudinal portion of the edge to and extending radially from the circumference and the only one longitudinal side of the outer surface of the chamber (5) and each side of the fastening strip being fastenable to a respective edge (4) of a hollow organ (18).

13. The closing means of claim 12, wherein the two-sided fastening strip (6) has a length greater than the length of the chamber (5).

14. The closing means of claim 12, wherein the chamber (5) is connected to at least one fluid port (14) through at least one tube (12).

15. The closing means of claim 12, wherein the closing means is formed from a single material.

16. The closing means of claim 15, wherein the single material comprises silicone.

17. The closing means of claim 12, wherein the chamber (5) is equally expandable and deflatable in all directions.

* * * * *